(12) United States Patent
Park et al.

(10) Patent No.: US 10,136,834 B2
(45) Date of Patent: Nov. 27, 2018

(54) NEURONAL RESONANCE MAGNETIC RESONANCE IMAGING METHOD

(71) Applicant: Korea Advanced Institute of Science and Technology, Daejeon (KR)

(72) Inventors: Sung-Hong Park, Daejeon (KR); Kwang Hyun Cho, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 974 days.

(21) Appl. No.: 14/583,279

(22) Filed: Dec. 26, 2014

(65) Prior Publication Data
US 2015/0238112 A1 Aug. 27, 2015

(30) Foreign Application Priority Data

Feb. 26, 2014 (KR) .......................... 10-2014-0022957
Jul. 3, 2014 (KR) .......................... 10-2014-0083007

(51) Int. Cl.
| | |
|---|---|
| *G01R 33/48* | (2006.01) |
| *A61B 5/055* | (2006.01) |
| *A61B 5/00* | (2006.01) |
| *G01R 33/483* | (2006.01) |

(52) U.S. Cl.
CPC ............ *A61B 5/055* (2013.01); *A61B 5/4064* (2013.01); *A61B 5/7257* (2013.01); *G01R 33/483* (2013.01); *G01R 33/4806* (2013.01)

(58) Field of Classification Search
CPC .................................................. G01R 33/483
USPC ........................................................ 324/309
See application file for complete search history.

(56) References Cited

U.S. PATENT DOCUMENTS

| | | | |
|---|---|---|---|
| 6,181,134 B1* | 1/2001 | Wald | G01R 33/485 324/307 |
| 6,486,669 B1 | 11/2002 | Sinkus et al. | |
| 7,840,250 B2 | 11/2010 | Tucker | |
| 9,612,306 B2* | 4/2017 | Lin | G01R 33/483 |

FOREIGN PATENT DOCUMENTS

| | | |
|---|---|---|
| KR | 1020040044155 | 5/2004 |
| KR | 1012971430000 | 8/2013 |
| KR | 1013107500000 | 9/2013 |

* cited by examiner

*Primary Examiner* — Reena Aurora
(74) *Attorney, Agent, or Firm* — Mayer & Williams, PC; Stuart H. Mayer

(57) ABSTRACT

The present disclosure provides a neuronal resonance-magnetic resonance imaging (NR-MRI) method and technology for measuring a difference between a resting state and a state of providing external stimuli with respect to various frequency bands by using the NR-MRI scheme through frequency band selection filter characteristic mapping of neurons. In addition, the present disclosure provides technology for revealing a frequency selective communication mechanism between brain regions on the basis of systems biology researches for the frequency selective communication mechanism between the brain regions as well as technology useful for completing proof-of-concept and a frequency selective communication map between the entire brain regions.

14 Claims, 11 Drawing Sheets

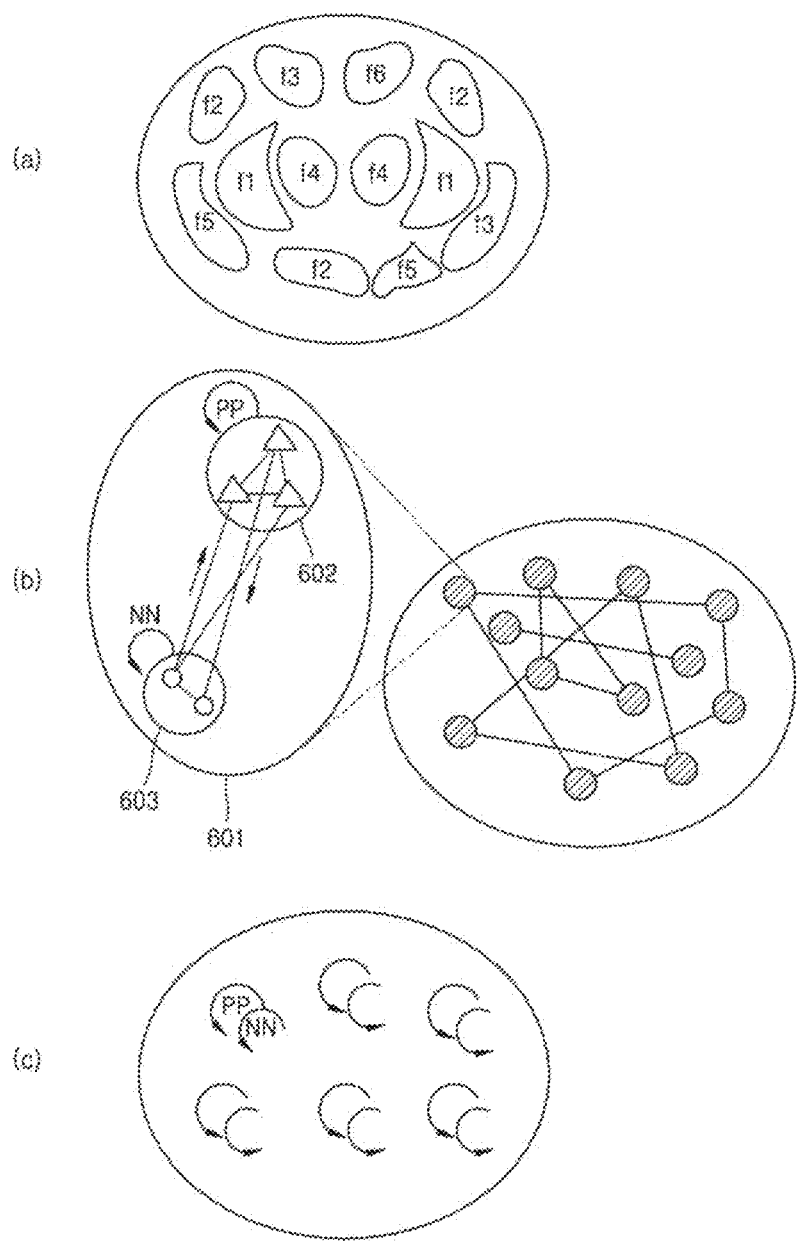

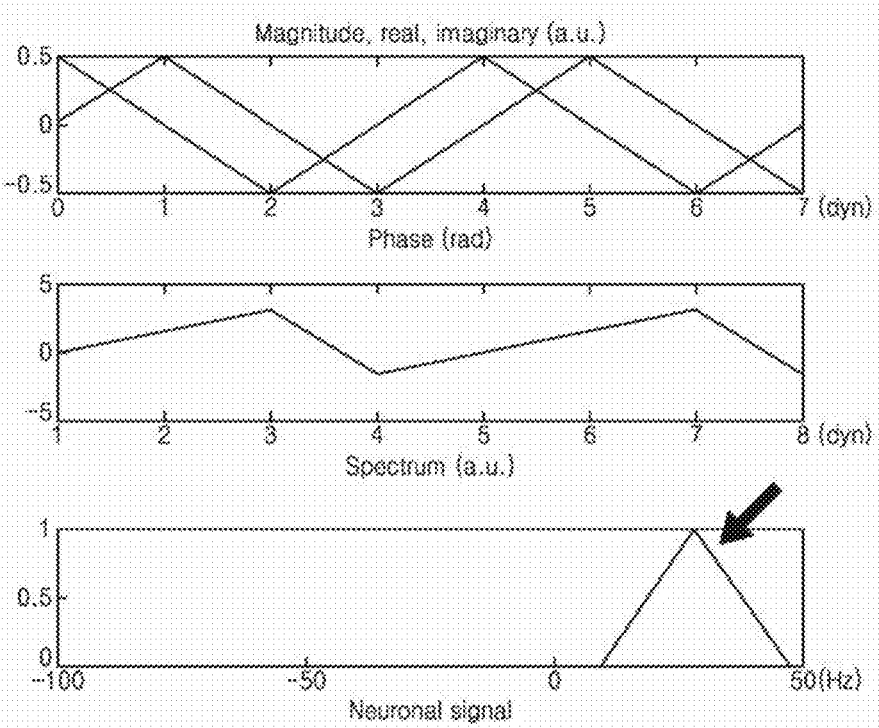

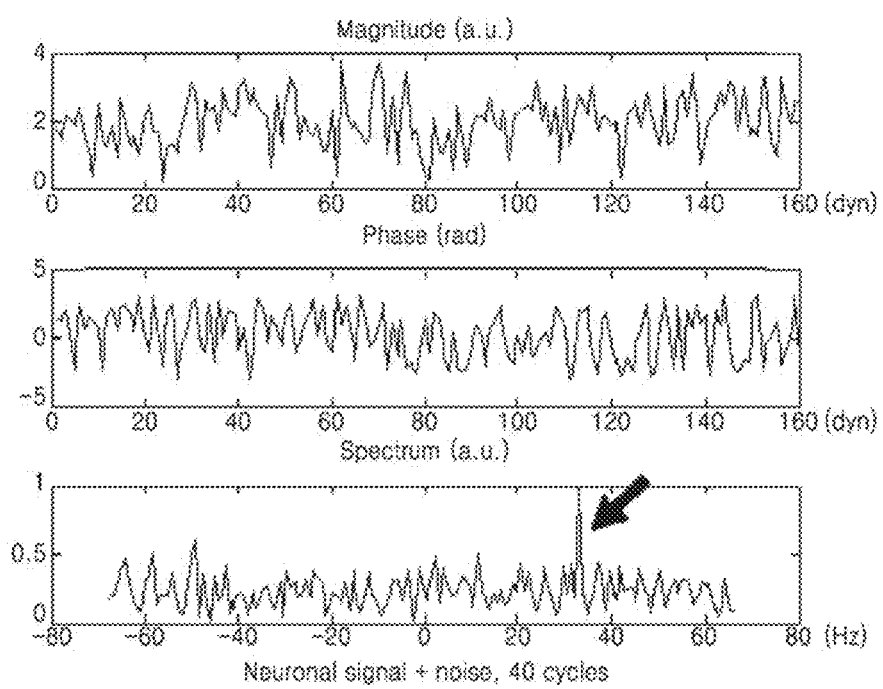

NEURONAL RESONANCE MAGNETIC RESONANCE IMAGING METHOD

CROSS-REFERENCE TO RELATED APPLICATION

This application claims priority to Korean Patent Application No. 10-2014-0022957 filed on Feb. 26, 2014 and Korean Patent Application No. 10-2014-0083007 filed on Jul. 3, 2014 and all the benefits accruing therefrom under 35 U.S.C. § 119, the contents of which are incorporated by reference in their entirety.

FUNDING STATEMENT

This invention was supported by Samsung Research Funding Center of Samsung Electronics under Project Number SRFC-IT1401-05.

BACKGROUND

The present disclosure relates to a method of acquiring and processing MRI data of neuronal resonance magnetic resonance imaging images.

It is obvious that communication is performed for delivering information between brain regions of a human. However, it is not still known how a specific brain region selectively delivers information to another brain region. In recent systems biology researches, a hypothesis is proposed that communication between brain regions is selectively performed through a frequency band selection filter from a signal of the entire brain. On the basis of this hypothesis, once a new imaging scheme capable of measuring a neuronal resonance frequency for the communication between the brain regions is developed, a communication mechanism between the brain regions, which is not yet well known, can be uncovered and have a significant effect on brain researches including psychology, mental science, and pathology.

A brain includes small regions responsible for numerous functions and these brain regions are structurally connected to each other. Most of brain functions such as actions, perceptions, and awareness are performed by fast and flexibly recombining a brain network. Recent researches partly reveal a dynamic, flexible and functional network configuration of the brain network on perceptions and awareness, selective concentration, and working memories. It has been known that oscillation characteristic and synchronization of neuronal spiking is associated with dynamic and flexible connectivity between brain regions. According to recent researches, it becomes revealed that neuronal oscillation and synchronization occurring in a specific frequency band controls a flow of information between the structurally connected brain regions and enables flexible and selective communication. However, it is not yet revealed through what mechanism the brain's flexible and selective communication tuned to a specific frequency band occurs in resting and active/stimulated states. Furthermore, according to numerous clinical data, it becomes known that patients of brain diseases including autism, schizophrenia, epilepsy, dementia, and Parkinson's disease have their neuronal synchronization characteristic changed in a wide frequency band and such abnormal neuronal synchronization may be a cause of symptoms (abnormal perceptions, actions, and movements, and the like) of those diseases.

Therefore, understanding of the selective communication mechanism between brain regions through the synchronization may allow a very important clue to treatment of the organic pathology and brain diseases to be discovered. Furthermore, developing a new imaging scheme capable of mapping a neuronal resonance characteristic for a wide band frequency used for brain region communication to a high resolution image may bring great ripple effects on academic, industrial and medical worlds related to medical and biological engineering.

On the other hand, a functional magnetic resonance imaging (fMRI) indirectly measures brain activities through interactions between neurons and blood flows, rather than measuring directly through a neuronal current. A couple of decades ago, it was shown for the first time that the fMRI might map non-invasively neuronal activities in the brain. Since then, the fMRI has had significant effects on neurology, psychology, and psychopathology.

The fMRI, unlike the existing MRI, is a mapping technique of a brain region by repetitively acquiring images when, and before and after there is external stimuli, and showing correlation with temporal patterns of the corresponding external stimuli through statistical processing. The fMRI is a nearly unique imaging scheme which is non-invasive and capable of mapping to a relatively high resolution image.

Even though the fMRI is a particular imaging scheme capable of non-invasively mapping neuronal activities, it uses an indirect measuring method through a blood flow change caused by neuronal activities rather than measuring directly a neuron's electrical signal. Endeavors to directly measure the neuron's electrical signal by using the MRI has been made for the last 10 years or more, but possibility thereof has been controversial.

About 10 years ago, it showed for the first time that the fMRI might be performed without external stimuli. This new fMRI technique is called as resting-state fMRI. A basic assumption of the resting-state fMRI is that if there is functional connectivity between two regions of the brain, temporal changes of MRI signals may have correlation with each other. The resting fMRI measures functional connectivity between brain regions. In the resting-state fMRI, a stimulation pattern used in the existing fMRI scheme is replaced with a temporal signal change of a seed region and a statistical analysis method is performed on whether rest of the brain regions shows a similar signal change to that of the corresponding brain region. In the resting-state fMRI scheme it is collectively measured whether certain brain regions (e.g., default mode network) are functionally connected. However, the existing fMRI scheme including the resting-state fMRI indirectly measures neuronal activities through blood flow dynamic reactions in a local region. The blood flow dynamic reaction is slow and has a time delay of about 4 seconds. Even though showing functional connectivity between brain regions, the resting-state fMRI does not show through what mechanism the brain regions selectively communicates. This is a fundamental limitation of the existing fMRI and explains why "frequency selective neuronal resonance" may not be confirmed with an existing method.

Furthermore, whether to be measurable a neuronal current in a living body by using the existing MRI imaging schemes has been controversial for the last ten years or more. Attempts to directly measure the neuronal current have been continuously made several times. Even though promising results have been continuously shown in phantom, cell culture, and theoretical calculation researches, whether to be measurable neuronal current in a living body by using MRI has been controversial for ten years or more. Researchers in the field of the art all agree on a fact that the neuronal current causes a magnetic field change on the periphery and the change may be measured with MRI. However, many researchers insist that it is very difficult to consistently measure the magnetic change in a living body with MRI because an MRI signal generated by a change of the magnetic field, which is generated by the neuronal current, is too small.

MRI schemes for directly detecting the neuron's electrical signal are largely divided into two approaches. A first approach is to use periodic stimulation having a uniform time period and measure the neuron's electrical signal by acquiring an MRI signal right after stimulation is completed (i.e., before blood flow dynamic reaction is generated). A second approach is to raise temporal resolution 100 ms) of MRI image acquisition and search for a component resonated with a frequency of external stimuli through Fourier transform. All the two approaches depend on a period or a frequency of external stimuli and do not consider the natural frequency of the neuron. Whether to detect a neuronal current signal is still controversial with respect to all the existing MRI imaging schemes including the two approaches.

SUMMARY

The present disclosure provides a neuronal resonance-magnetic resonance imaging (NR-MRI) method.

The present disclosure also provides technology for measuring a difference between a resting state and a state of providing external stimuli with respect to various frequency bands by using the NR-MRI scheme through frequency band selection filter characteristic mapping of neurons.

The present disclosure also provides technology for revealing a frequency selective communication mechanism between brain regions on the basis of systems biology researches for the frequency selective communication mechanism between the brain regions.

The present disclosure also provides technology useful for completing proof-of-concept and a frequency selective communication map between the entire brain regions.

In accordance with an exemplary embodiment, a magnetic resonance signal processing method is provided which uses a process for obtaining magnetic resonance imaging (MRI) data with an MRI scheme using a gradient magnetic field pattern for detecting a magnetic field oscillation signal. The method includes acquiring a plurality of MRI data by repeating the process a plurality of times while changing relative phases between the gradient magnetic field pattern and the magnetic field oscillation signal; and calculating frequency characteristics from the acquired plurality of pieces of MRI data according to a pre-determined rule, wherein the plurality of MRI data are K-space data or MRI image data.

At this point, the magnetic field oscillation signal may be a signal having an unknown generation period and an unknown phase at a specific time.

The magnetic field oscillation signal may include a specific frequency component.

The pre-determined rules may be Fourier-transforming signals of the acquired plurality of pieces of MRI data arrayed on a time-axis according to the relative phases.

The obtaining of the MRI data may use an acquiring process for acquiring N pieces of the MRI data by repeating the process with respect to pre-determined N relative phases between the gradient magnetic field pattern signal and the magnetic field oscillation signal and may include acquiring the plurality of pieces of MRI data by sequentially repeating the acquiring process M times along time.

The pre-determined rule may be Fourier-transforming signals of the acquired plurality of pieces of MRI data arrayed on a time-axis according to the relative phases.

The plurality of pieces of MRI data may be temporally divided, and each of the divided data may be Fourier-transformed to acquire time-axis data with respect to a neuronal signal change.

The specific frequency may be identical to a frequency of the gradient magnetic field pattern.

The pre-determined rule may be finding a value about the specific frequency among frequency components of the acquired plurality of MRI data.

The acquiring of the MRI data may include a acquiring process for acquiring N pieces of MRI data by repeating the process for the pre-determined N relative phases between the gradient magnetic field pattern signal and the magnetic field oscillation signal, and differences between the N relative phases may satisfy integer multiples of $2*\pi/N$ with respect to the specific frequency.

A time to repeat (TR) among MRI parameters may be adjusted for making the differences between the N relative phases into integer multiples of $2*pi/N$ with respect to the specific frequency.

The magnetic field oscillating signal may be a neuronal signal.

The gradient magnetic field pattern may be an oscillatory gradient magnetic field pattern.

The oscillatory gradient magnetic field pattern may be a bipolar readout gradient pattern using in a multi-echo gradient echo imaging method.

Spatial directivities of the gradient magnetic field pattern may be different with respect to two different repeatedly performed processes.

In accordance with another exemplary embodiment, an MRI apparatus uses a process for obtaining MRI data with an MRI scheme using a gradient magnetic field pattern signal for detecting a magnetic field oscillation signal resonating with a specific frequency and having an unknown generation period and an unknown phase at a specific time. The MRI apparatus performs obtaining a plurality of MRI data by repeating the process a plurality of times while changing relative phases between the gradient magnetic field pattern signal and the magnetic field oscillation signal; and calculating frequency characteristics from the obtained plurality of MRI data according to a pre-determined rule.

In accordance with another exemplary embodiment, a non-transitory computer readable medium having a program recorded thereon, which, when executed by an MRI apparatus, performs a method includes: using a process for obtaining MRI data with an MRI scheme using a gradient magnetic field pattern signal for detecting a magnetic field oscillation signal resonating with a specific frequency and having an unknown generation period and an unknown phase at a specific time; obtaining a plurality of MRI data by repeating the process a plurality of times while changing relative phases between the gradient magnetic field pattern signal and the magnetic field oscillation signal; and calculating frequency characteristics from the obtained plurality of MRI data according to a pre-determined rule.

In accordance with another exemplary embodiment, a magnetic resonance signal processing method uses a process for obtaining MRI data with an MRI scheme using an oscillatory gradient magnetic field pattern signal having a pre-determined oscillation frequency for detecting a magnetic field oscillating signal having an unknown generation period and an unknown phase at a specific time. The method may use a first process including acquiring a plurality of MRI data by repeating the process a plurality of times while changing relative phases between the oscillatory gradient magnetic field pattern signal and the magnetic field oscillation signal; and calculating a value about the pre-determined oscillation frequency from the acquired plurality of pieces of MRI data according to a pre-determined rule. In addition, the method may include acquiring P values about the pre-determined oscillation frequency with respect to the first process by performing the first process P times for allowing the pre-determined oscillation frequency to have P different values.

In accordance with another exemplary embodiment, a neuronal resonance magnetic resonance imaging method includes: performing a first process for obtaining an image with an MRI scheme having an oscillatory gradient magnetic field pattern for detecting a neuronal signal resonating with a specific frequency; performing a second process for acquiring a plurality of MRI images by repeating a second step M times, the second step obtaining respective MRI images for N different neuronal resonance phases by repeating the first process N times; and performing a third process for calculating and spectrally analyzing through Fourier-transforming an entirety of or a part of the plurality of multi-phase MRI images according to a pre-determined rule.

The specific frequency may be identical to a frequency of the gradient magnetic field pattern signal.

In the third process, the pre-determined rule may find a neuronal component resonating with the specific frequency among frequency components of the multi-phase data.

Differences between the N neuronal resonance phases may satisfy integer multiple of $2*\pi/N$.

A time to repeat (TR) among MRI image parameters may be adjusted for making differences between the N neuronal resonance phases into the integer multiple of $2*\pi/N$.

In the third process, the plurality of pieces of MRI data may be temporally divided, and each of the divided data may be Fourier-transformed to acquire time-axis data with respect to a neuronal signal change.

The oscillatory gradient magnetic field pattern may be a bipolar readout gradient pattern using in a multi-echo gradient echo imaging method.

The oscillatory gradient magnetic field pattern may be applied in various spatially different directions such as X, Y, and Z.

According to another aspect of the present invention, an MRI apparatus includes an MRI image acquiring unit and a processing unit controlling an operation of the MRI image acquiring unit. The processing unit may be configured to perform a first process for obtaining an image with an MRI scheme having an oscillatory gradient magnetic field pattern for detecting a neuronal signal resonating with a specific frequency; performing a second process for acquiring a plurality of MRI images by repeating a second step M times, the second step obtaining respective MRI images for N different neuronal resonance phases by repeating the first process N times; and performing a third process for calculating and spectrally analyzing through Fourier-transforming an entirety of or a part of the plurality of multi-phase MRI images according to a pre-determined rule.

In accordance with another exemplary embodiment, a computer readable medium having a program recorded thereon, which, when executed by an MRI apparatus, performs a method includes: performing a first process for obtaining an image with an MRI scheme having an oscillatory gradient magnetic field pattern for detecting a neuronal signal resonating with a specific frequency; performing a second process for acquiring a plurality of MRI images by repeating a second step M times, the second step obtaining respective MRI images for N different neuronal resonance phases by repeating the first process N times; and performing a third process for calculating and spectrally analyzing through Fourier-transforming an entirety of or a part of the plurality of multi-phase MRI images according to a pre-determined rule.

In accordance with another exemplary embodiment, a method of processing MRI time series acquisition data includes performing a first process for including a first step for acquiring an MRI data set by using an oscillatory gradient magnetic field pattern signal having a pre-determined frequency and performing acquiring N MRI data sets by repeating the first step N times for one period of the oscillatory gradient magnetic field pattern signal; performing a second process for acquiring time-axis data representing an energy change over time of a signal mapped to a first image region by calculating energy of a signal mapped on the first image region of an entire image represented by each of the MRI data sets with respect to the N MRI data sets; and performing a third process for calculating a value about the specific frequency component among frequency components of the time axis data according to a pre-determined rule.

The third process may include Fourier-transforming the time axis data.

The specific frequency may be identical to a frequency of the oscillatory gradient magnetic field pattern signal.

The N MRI data sets may be data obtained with respect to a neuronal space.

Differences between the N neuronal resonance phases may satisfy integer multiple of $2*\pi/N$.

The second and third processes are repetitively performed with respect to the first image region and a second image region of the entire image, results of which are stored.

The first process is repeated M times, and, by using M pieces of results data obtainable from the M times repetition, the second and third processes are repeated M times.

In the first process, a plurality of MRI data sets are acquired by repeating the first process M times during M periods of the oscillatory gradient magnetic field pattern signal. In the second process, time-axis data are acquired which represents an energy change over time of a signal mapped to a first image region by calculating energy of a signal mapped to the first image region of an entire image, which each of the MRI data sets represents with respect to the plurality of MRI data sets. In the third process, a value about a specific frequency component among frequency components of the time axis data acquired during the M periods are calculated by the pre-determined rule.

The oscillatory gradient magnetic field pattern signal may be a bipolar readout gradient pattern signal using in a multi-echo gradient echo imaging method.

BRIEF DESCRIPTION OF THE DRAWINGS

Exemplary embodiments can be understood in more detail from the following description taken in conjunction with the accompanying drawings, in which:

FIGS. 3A, 3B and 3C are schematic diagrams for an experimental research on NR-MRI in accordance with an exemplary embodiment.

FIGS. 4A, 4B, 4C, 4D, 4E and 4F are graphs representing simulation results of NR-MRI in accordance with exemplary embodiments.

DETAILED DESCRIPTION OF EMBODIMENTS

Hereinafter, specific embodiments will be described in detail with reference to the accompanying drawings. However, the present invention is not limited to embodiments described herein and can be implemented in various other forms. Terms used herein are for assisting in comprehensive understanding of exemplary embodiments and are not intended to limit the scope of the present invention. In addition, it is to be understood that the singular forms "a," "an," and "the" include plural referents unless the context clearly dictates otherwise.

Hereinafter, NR-MRI is described according to an embodiment of the present invention with reference to FIGS. 1 to 4F.

Figure 1:
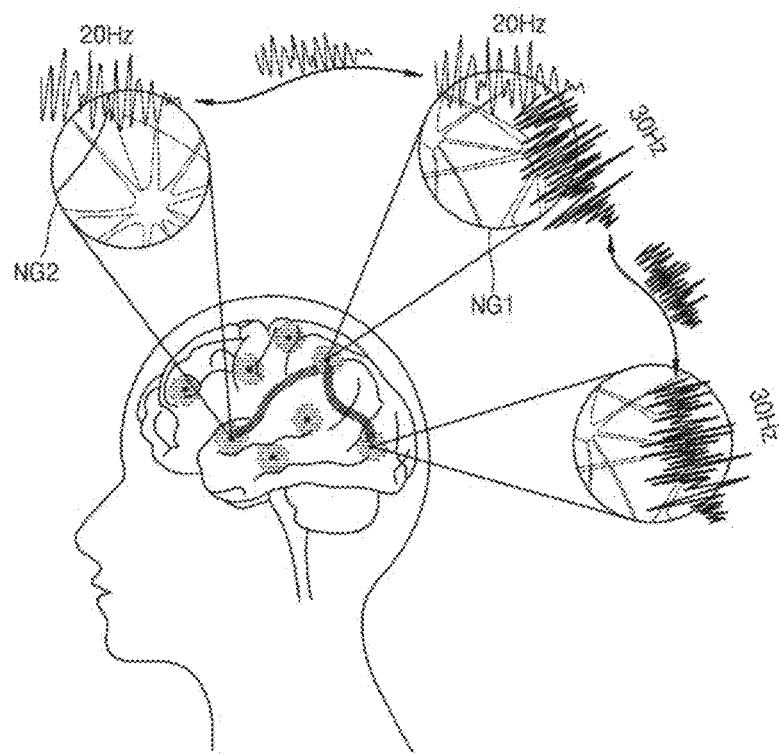
FIG. 1 illustrates frequency selective communication between brain regions in neuronal resonance-magnetic resonance imaging (NR-MRI) in accordance with an exemplary embodiment.

FIG. 1 illustrates frequency selective communication between brain regions in NR-MRI according to an embodiment of the present invention.

The brain of a mammal shows resonance in a neuron group due to interaction between neurons. As illustrated in FIG. 1, one neuron group NG1 resonates with a specific frequency and selectively communicates with another neuron group NG2 resonating with the same frequency.

Accordingly, the present invention provides NR-MRI scheme capable of measuring a frequency selective communication signal between brain regions.

Figure 2A:
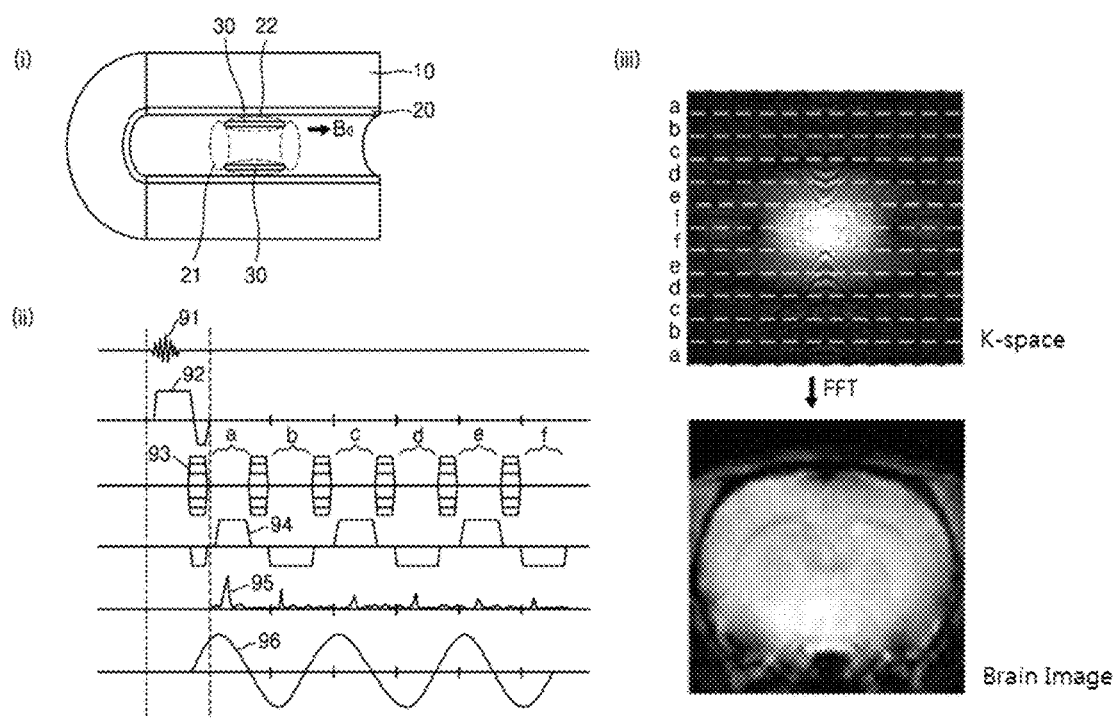
FIGS. 2A, 2B and 2C are schematic diagrams for NR-MRI in accordance with exemplary embodiments.
Figure 2B:
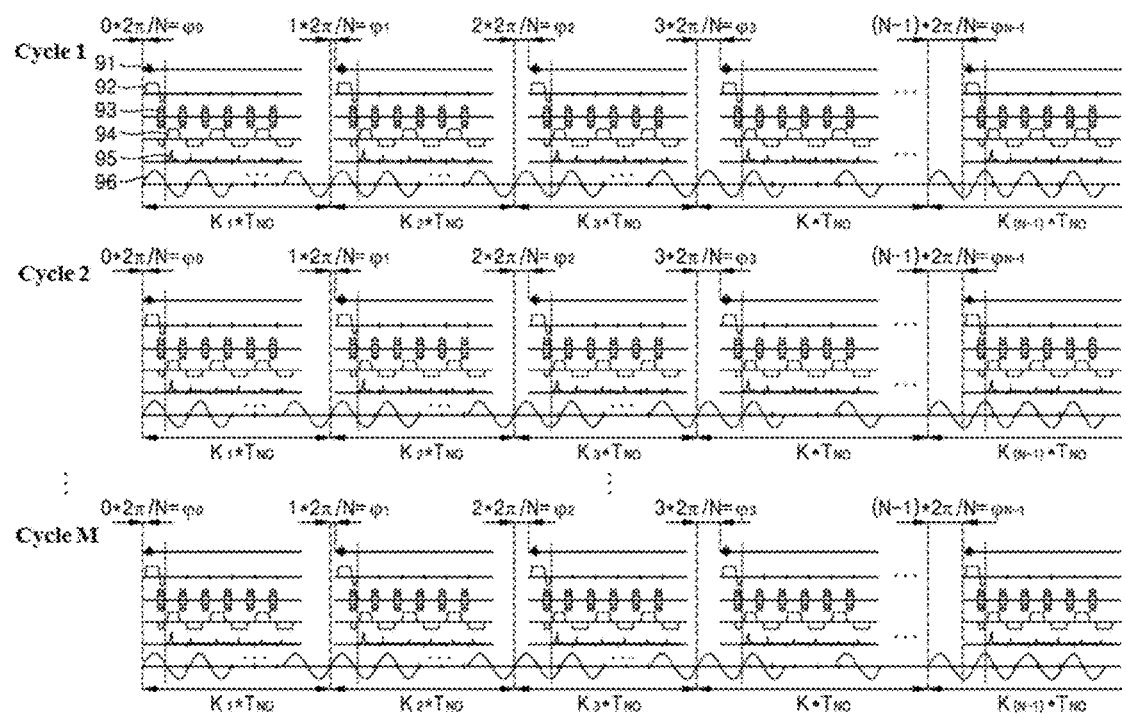
Figure 2C:
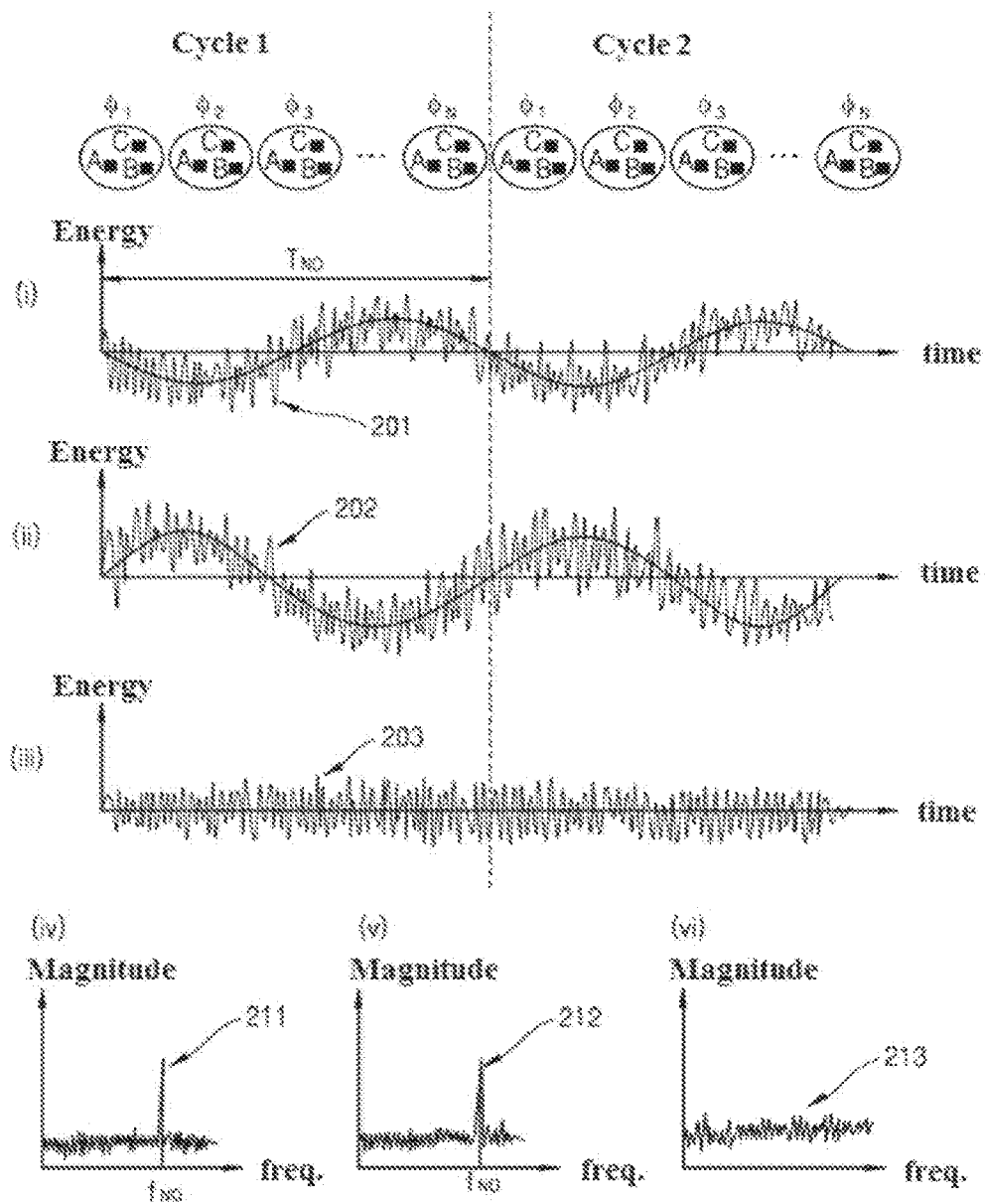

FIGS. 2A to 2C are schematic diagrams for NR-MRI according to embodiments of the present invention. FIG. 2A is a pulse diagram of the NR-MRI, FIG. 2B is schematic diagrams for multi-phase measurement method (left) and temporal signal changes and Fourier analyses (right) according to the multiple phases, and FIG. 2C is schematic diagrams for phase-insensitive oscillation detection of neurons.

Here, in FIG. 2A, (i) is a schematic diagram for an NR-MRI system, (ii) is a pulse sequence for multi-echo-gradient echo (ME-GE) able to be used for the NR-MRI system, and (iii) illustrates an example of photo and image of a corresponding K-domain.

In (i) of FIG. 2A, the NR-MRI system may include a superconducting magnet 10, a gradient coil 20, a gradient coil-Z 21, a gradient coil-Y 22, and an electric wave transmitting and receiving coil 30.

In (ii) of FIG. 2A, graphs 91 to 96 respectively represent an RF signal 91 transmitted by the electric wave transmitting and receiving coil 30, a gradient Z signal pulse 92, a gradient Y pulse 93, a gradient X pulse 94, an RX signal 95 received by the electric wave transmitting and receiving coil 30, and a neuronal resonance waveform 96 of a living organism disposed in the NR-MRI system.

(iii) of FIG. 2A represents an example of the K-domain constructed by using the RX signal 95 received in (ii) of FIG. 2A and an example of a brain image generated by fast-Fourier-transforming (FFT) the K-domain.

According to FIG. 2A, in the ME-GE, a resonance frequency of a bipolar readout gradient magnetic field may be matched with the neuronal resonance frequency, and may fill a central portion of the K-domain because an echo signal obtained later resonates longer with the neurons and reflects a stronger neuronal signal.

In the multi-phase measurement method of NR-MRI illustrated in FIG. 2B, a time to repeat (TR) is set in order for a temporal phase of neuronal resonance compared to MRI image acquisition to be increased by $2\pi/N$, where N is the number of multi-phases, for every TR.

According to FIG. 2B, the multi-phase measurement method may be repetitively performed by M cycles. For each cycle, a pulse sequence for the ME-GE may be repeated N times and provided. Hereinafter, a method is described which provides the pulse sequence for the ME-GE in each cycle.

While the multiple phase measurement method is performed, the neuronal resonance waveform 96 is assumed to have a period of $T_{NO}$. At this point, the pulse sequence may be provided to satisfy the following two conditions in an embodiment of the present invention. First, a period of the pulse sequence that is repeated N times and provided is set to be identical to the period of $T_{NO}$ of the assumed neuronal resonance waveform 96. Second, a generation time of (i)-th pulse sequence of the N times repeated and provided pulse sequence is allowed to be delayed by $K*T_{NO}+2\pi/N$ from a generation time of (i−1)-th pulse sequence, where i=2 to N. Here, $K*T_{NO}$ means an integer multiple of the resonance period of the neuronal resonance waveform 96. In this way, phases of the N times repeated pulse sequence for the neuronal resonance waveform 96 become differed. This may be denoted herein as 'multi-phases'. For example, in FIG. 2A, a generation time of (i)-th pulse sequence becomes delayed by $i*2\pi/N$ from the zero-crossing time when the neuronal resonance waveform 96 heads from negative to positive In other words, a phase difference of $\phi_i=i*2\pi/N$ exists between the (i)-th pulse sequence and the neuronal resonance waveform 96.

At this point, FIG. 2C represents results obtainable in a case where, for example, the period of the pulse sequence is $T_{NO}$ according to the multi-phase measurement method, the neuronal resonance period is $T_{NO}$ in regions A and B of the brain, and a neuronal resonance period in the brain region C is different from $T_{NO}$. At this point, neurons in the brain region C do not resonate.

Graphs 201, 202, and 203 of (i), (ii) and (iii) of FIG. 2C respectively represent magnitudes of energies according to time, which are obtained with the multi-phase measurement method with respect to the brain regions A, B, and C. The graphs 201 and 202 may have periodicity for the brain regions A and B, but the graph 203 may not have periodicity for the brain region B.

(iv), (v), and (vi) of FIG. 2C respectively represent graphs 211, 212, and 213 obtained by performing FFT on the graphs 201, 202, and 203 of (i), (ii), and (iii) in FIG. 2C. In the graphs 211 and 212, the resonance frequency is $f_{NO}$, but there is no any particular resonance frequency in the graph 213. Consequently, it may be known that the brain regions A and B are regions in which the period of the pulse sequence resonates with the same frequency as $T_{NO}$ by interpreting (iv), (v), and (vi) in FIG. 2C.

Referring to FIGS. 2A to 2C, the NR-MRI according to an embodiment of the present invention may maximize the MRI signal change in neurons by applying a gradient magnetic field oscillating with the neuronal resonance frequency to the MRI scheme.

The existing MRI schemes for directly detecting the neuronal electrical signal have largely two issues. First, an MRI signal change is too small, and second, the neuronal resonance nearly randomly occurs without regularity in temporal phase and period. Accordingly, the NR-MRI scheme according to an embodiment of the present invention is intended to address the issues by repetitively performing multi-phase measurement tuned to the neuronal resonance frequency and then applying Fourier analysis thereto.

There have been attempts to detect the neuronal resonance with the MRI scheme, but possibility thereof has been controversial for the last 10 years. One of the most important reasons is that the MRI signal change by neuronal resonance is very small. Another important issue is that since temporal period and phase in which the neuronal resonance occurs are random and are never known, MRI image acquisition and synchronization are nearly impossible. Another issue is that since neurons periodically resonate, there is high probability that the neurons resonate once or more while RF energy is transmitted and received for acquiring MRI images. In this case, the time when the RF signal is transmitted and received in an MRI system is after the MRI signal change by the neuronal resonance is nearly cancelled. Due to the above-described issues, possibility of the existing methods is considered as controversial.

The NR-MRI scheme according to an embodiment of the present invention, as a new MRI imaging method for directly detecting the neuronal resonance with an MRI system, includes largely three elements. Three elements of the new MRI imaging method includes (i) applying a gradient magnetic field pattern resonating with the neuronal resonance frequency to the MRI imaging scheme, (ii) repetitively obtaining multi-phase signals tuned to the neuronal resonance frequency, and (iii) applying Fourier analysis to separate a frequency component corresponding to the neuronal resonance frequency. In other words, according to the NR-MRI scheme according to an embodiment of the present invention, other undesired signals, for example, a hemodynamic response, errors of an MRI system such as motions or flows, harmonic frequency components between the neuronal resonance frequency and a resonance frequency of a gradient magnetic field current, and noises are filtered out and only desired resonance frequency component may be separated.

In order to implement the NR-MRI scheme according to an embodiment of the present invention, neuronal-resonance oscillating gradient (NROG) magnetic field may be combined with several MRI schemes, including multi-echo gradient echo (ME-GE), spin-echo echo planar imaging (SE-EPI), and gradient echo (GE) methods. According to FIG. 2A, all the MRI systems have three gradient magnetic field coils and enable obtaining spatial image information, namely, imaging by allowing the three gradient magnetic field coils to linearly modulate a magnitude of a magnetic field in three directions in the MRI system. The SE-EPI and the GE may be implemented by using independent "NROG" magnetic field and perform mapping of the neuronal resonance frequency characteristic according to directivity. In an embodiment of the present invention, a method is mainly described which uses, as the "NROG" magnetic field, a bipolar readout gradient pattern originally existed in the ME-GE method instead of the SE-EPI or GE method.

In order to construct the "NROG" magnetic field pattern, an echo spacing time (ESP) between two adjacent echoes is made to be the same as a half of the neuronal resonance frequency according to the following Equation (1) in the ME-GE method.

$$T_{NO}(\text{neuronal resonance period})=2*ESP=\text{period of a bipolar readout gradient pattern} \quad (1)$$

In ME-GE method, since used for creating one MRI image, the multi-echoes may be used for reducing an imaging time. According to FIG. 2A, as the neurons resonate and the gradient magnetic field oscillates, an MRI signal change becomes larger and echo data obtained later becomes to have a stronger neuronal resonance signal. Accordingly, at the time of configuring a K-space, it is advantageous that the later obtained echo data is allowed to occupy the central portion thereof, while initially obtained echo data is allowed to occupy edges thereof.

However, since the magnitude of the echo signal exponentially decreases according to a time constant called as T2* (typically <80 ms), it is necessary to balance two conflicting effects (an aspect that a neuronal resonance signal is accumulated and increased, and a phenomenon that the signal exponentially decreases according to T2*). Finally, the number of multi-echoes in the ME-GE scheme is required to be optimized through experiments and simulations with respect to various factors, namely, a magnitude of a main magnetic field, spatial resolution, and a resonance frequency desired to see, and the like.

A neuronal resonance of a frequency $f_{NO}$ may be expressed as Equation (2).

$$S_{NO}=A*\cos(2\pi*f_{NO}*t+\phi)+S_0 \quad (2)$$

If, as shown in FIGS. 2A to 2C, a neuronal resonance phase $\phi$ is the same as a phase of the MRI oscillatory gradient magnetic field pattern, the MRI signal change by the neurons would be maximized. However, since the neuronal resonance phase is created randomly, MRI data acquisition is required to be repetitively obtained with multi-phases compared to the neuronal resonance phase and the result is required to be analyzed with the Fourier analysis. One of methods for obtaining data with the multi-phases in the ME-GE method is to designate a time to repeat (TR) as the following Equation (3) and make a difference between the neuronal resonance phase and the MRI gradient magnetic field oscillating phase.

$$TR=(N_{Echoes}*ESP)+(2*ESP/N_{phases}) \quad (3)$$

where, $N_{Echoes}$ and $N_{phases}$ denote the number of multi-echoes and the number of multi-phases, respectively.

Here, $N_{Echoes}$ is required to be an even number. Equation (3) means that TR is a value that an integer multiple ($N_{Echoes}*ESP$) of the neuronal resonance period is summed to a value ($2*ESP/N_{phases}$) of a resonance period divided by the number of multiple phases. In Equation (3), the term ($N_{Echoes}*ESP$) of the integer multiple of the neuronal resonance frequency does not change the difference between phases of the neuron's phase and the oscillatory gradient magnetic field, but the value ($2*ESP/N_{phases}$) of the resonance frequency divided by the number of multiple phases increases the phase difference therebetween by $2\pi/N_{phases}$. The phase difference eventually increases by $27/N_{phases}$ for every TR, and this means the phase difference repetitively appears with $N_{phases}$ as a period when the multi-phase signal is repetitively obtained as shown in FIG. 2B. By repeating the multiple phase data acquisition, (i) K-space domain is fully filled and an MRI image is completed, (ii) the multi-phase MRI images are repetitively obtained and then the Fourier analysis may be applied.

In addition, as shown in FIG. 2C, a neuronal signal having a specific frequency becomes periodically changed at the time of the aforementioned repetitive multi-phase image acquisitions, and the neuronal signal may be precisely separated from other undesired signals because application of Fourier transform to a component thereof may allow a corresponding frequency component to be found. At this point, the Fourier analysis may be applied to all the repetitively obtained multi-phase data, but when the multi-phase data is temporally periodically divided by using a sliding-time window and the Fourier analysis is applied, a temporal change of the neuronal frequency characteristic may be seen. In addition, such a sliding-time window analysis also enables a brain frequency change to be seen according to a functional change when the brain is in a resting state or has external stimuli.

FIG. 3 is a schematic diagram for an experimental research of NR-MRI according to an embodiment of the present invention.

Since the difference between the neuron resonance phase and the image acquisition phase increases by $2\pi/N$ for every TR, when the multi-phase acquisition is repeated, the phase difference repetitively appears in a period of N (namely. $\phi_1$, $\phi_2$, ..., $\phi_N$, $\phi_1$, $\phi_2$, ..., $\phi_N$, $\phi_1$, $\phi_2$, ..., $\phi_N$)(See FIG. 2B). This allows the neuronal signal to appear in a resonated type with a period of N in the repetitively obtained multi-phase data (See (ii) and (iii) of FIG. 2C). When repetitive multi-phase data is present in each MRI image pixel existing in a space, and Fourier transform is performed in a repetitive multi-phase direction, a signal corresponding to a neuronal frequency determined by N may be extracted (See (iv) and (v) of FIG. 2C).

FIG. 3A illustrates an example of a mapping result of a neuronal resonance frequency distribution map by using NR-MRI scheme according to an embodiment of the present invention.

FIG. 3B illustrates an example of a result that a communication channel between the brain regions is derived through an algorithm optimizing a population simulation such as a Wilson-Cowan model. Such a communication channel map may be applied to reveal brain regions frequency-selectively communicating to each other. In FIG. 3C, a reference numeral 601 denotes a Wilson-Cowan model, a reference numeral 602 denotes an excitatory population, and a reference numeral 603 denotes an inhibitory population.

FIG. 3C shows an example of a result that a distribution map is constructed which shows various feedback loops are present in each brain region according to an embodiment of the present invention.

As shown in FIG. 3A to 3C, the aforementioned neuronal frequency mapping method may be applied to researches on neuronal resonance characteristics and a communication mechanism between brain regions according to a frequency band by applying for various frequencies. Such a communication mapping between the brain regions may be further developed and completed through systems biology.

The oscillatory gradient magnetic field pattern may increase a neuronal signal but one image acquisition may have a still small signal. Even though typically repetitive image acquisition increases a signal by an averaging effect, the neuron imaging scheme using the existing MRI schemes has little averaging effect. The reason is that a temporal phase and an occurrence/extinction interval of the neuronal resonance are random.

However, when applying repetitive multi-phase image acquisitions and Fourier analysis according to an embodiment of the present invention, a temporal average effect is valid and a neuronal signal to noise ratio may be improved without knowing the temporal phase and the occurrence/extinction interval. The NR-MRI scheme according to an embodiment of the present invention has 5 merits:

(1) Neuronal resonance mapping according to a frequency band is possible, which is not typically allowable.

(2) Advance information is not necessary on a neuronal resonance frequency, temporal phase and occurrence interval.

(3) Measurement in a resting state and measurement of a functional change at the time of having external stimuli are all possible.

(4) Implementation in all the existing MRI equipment is possible.

(5) A neuronal resonance component in a high frequency is advantageous to accelerate MRI image acquisition.

FIGS. 4A to 4F are graphs representing simulation results of NR-MRI according to embodiments of the present invention.

Figure 4B:
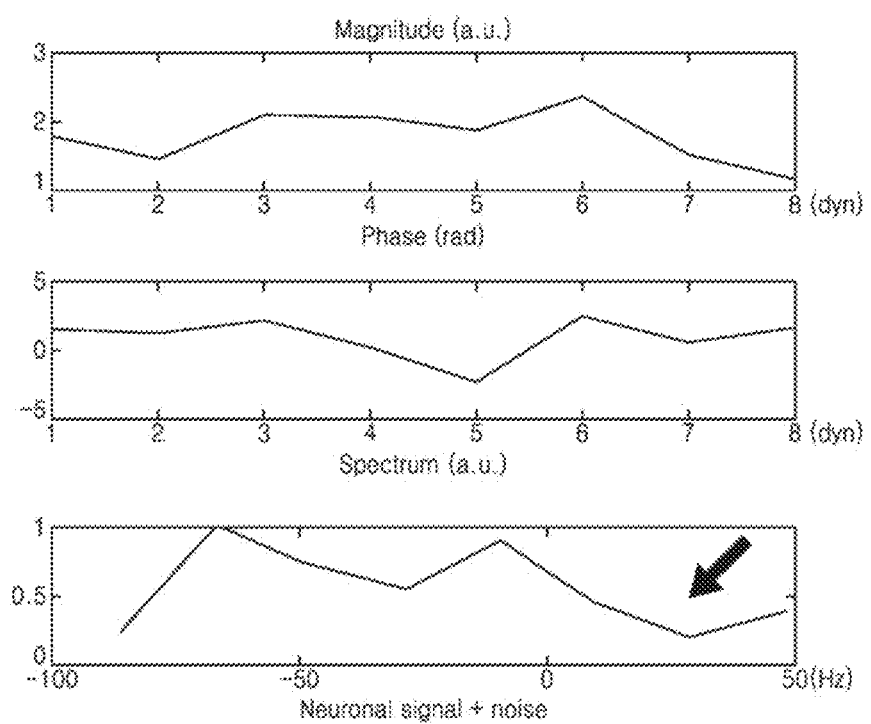
Figure 4D:
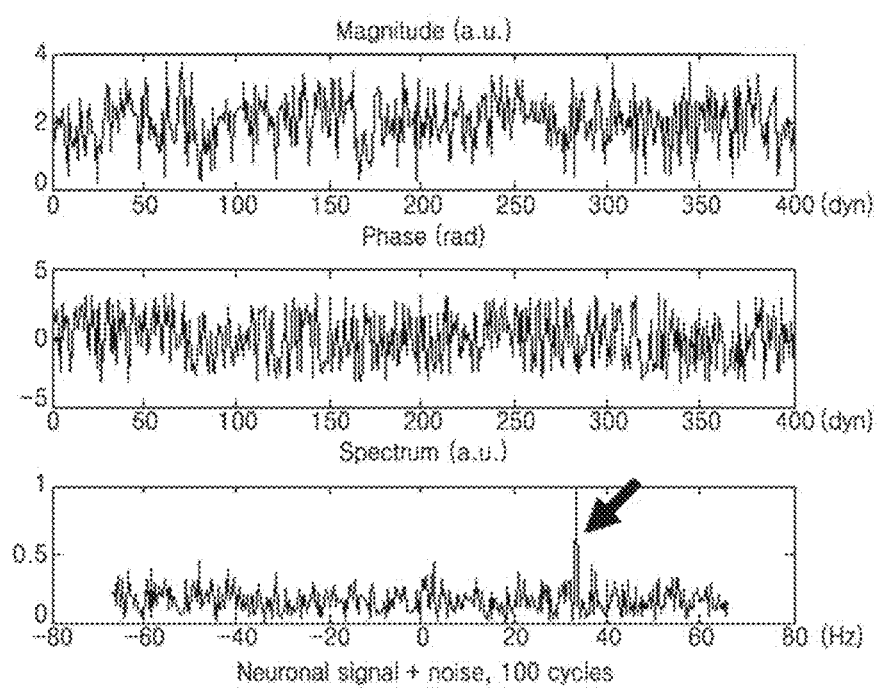
Figure 4E:
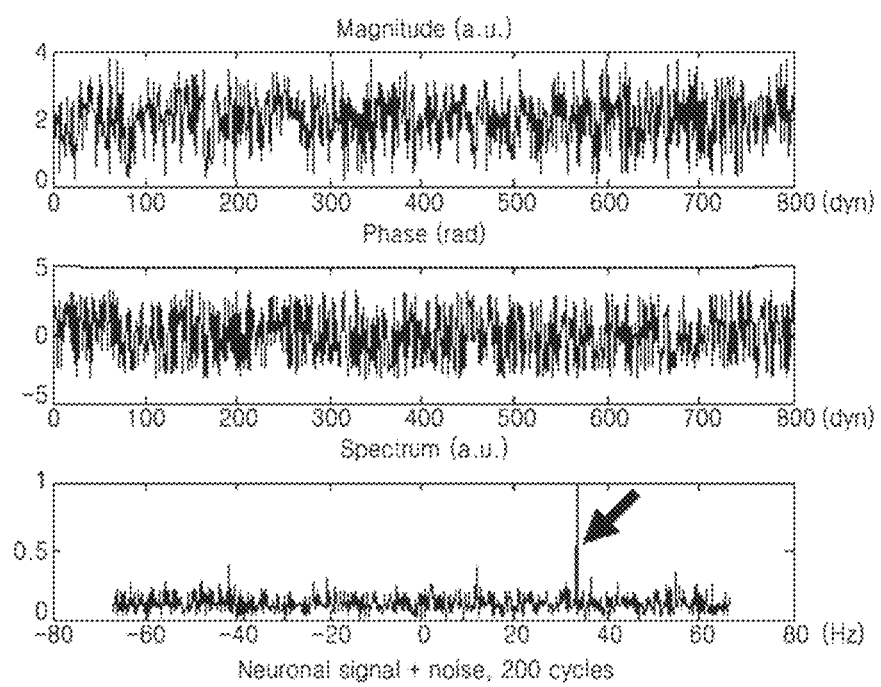
Figure 4F:
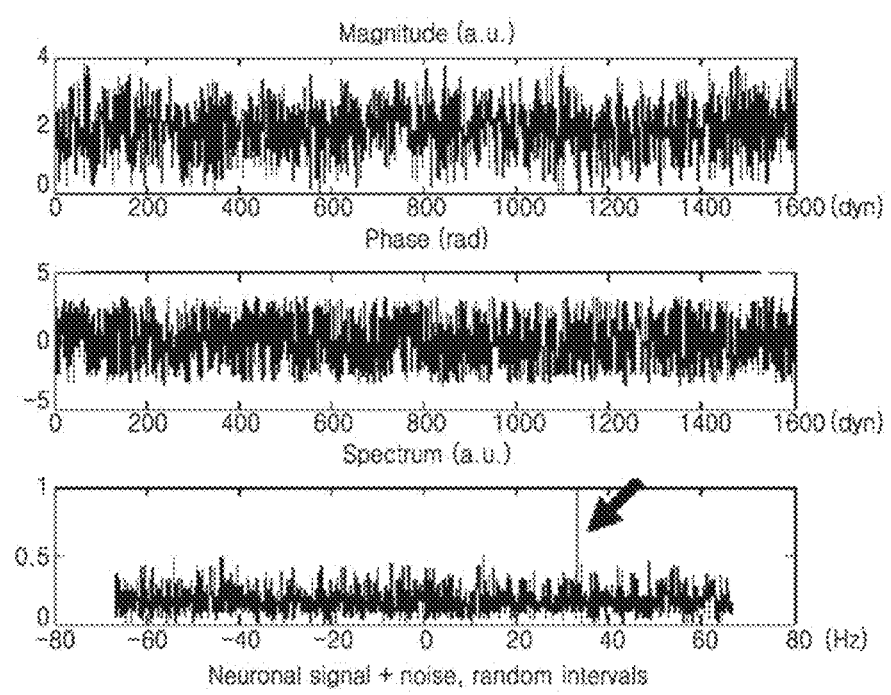

FIG. 4A represents a neuronal signal, FIG. 4B represents a neuronal signal+noise, FIG. 4C represents a result that "neuronal signal+noise" is repeated for 40 cycles, FIG. 4D represents a result that "neuronal signal+noise" is repeated for 100 cycles, FIG. 4E represents a result that "neuronal signal+noise" is repeated for 200 cycles, FIG. 4F represents data that a signal that "neuronal signal+noise" is repeated for 200 cycles and a signal that only "noise" is repeated for 200 cycles are cross-disposed randomly. In FIGS. 4A to 4F, the top portion of each graph represents a magnitude, the middle portion represents a phase and the bottom portion represents a spectrum. Arrows 41 to 46 denoted in FIG. 4A to 4F represent positions of the neuronal resonance frequency (33.3 Hz in a simulation according to an embodiment of the present invention).

Here, in the NR-MRI simulation according to an embodiment of the present invention, noise is five times stronger than the neuronal signal.

Simple simulation was performed in order to check repetitive multi-phase acquisitions and neuronal current detectability through Fourier analysis. As shown in FIG. 4A, an MRI signal created by neurons was assumed to be temporally represented as a sinusoidal curve and a frequency thereof is 33.3 Hz (it is also assumed that there is only a temporal phase change and no magnitude change). After five times higher complex random noise than the MRI signal of the neurons was added, as shown in FIG. 4B, it can be seen that a neuronal signal corresponding to 33.3 Hz completely disappeared from a spectrum appeared after Fourier transform. The task of FIG. 4B was repetitively applied for 40 cycles, a neuronal electrical signal corresponding to 33.3 Hz began to appear again as shown in FIG. 4C. At this point, when the number of cycles is increased, it can be seen that the noise becomes further reduced as shown in FIGS. 4D and 4E. Even after data ("noise") only formed of random noises was cross-disposed randomly between data ("signal+noise") as shown in FIG. 4E, it can be seen that a corresponding neuronal signal was detected in a spectrum after Fourier transform (the total number of cycles of "signal+noise" is the same as the total number of cycles of "noise").

In other words, as shown in FIGS. 4A to 4F, a magnitude and a phase signal are mostly determined by noise and a small signal of ⅕ by neurons is not nearly distinguished on a time axis. Such a characteristic is very similar to a characteristic of an actual MRI signal. The NR-MRI simulation according to an embodiment of the present invention is for a case where a neuronal MRI signal changes only in phase but not in magnitude, and may have a nearly similar result to that of a simulation performed under assumption that a neuronal MRI signal changes only in magnitude but not in phase (data is not shown). These results mean that measurement is possible in a case where the repetitive multi-phase measurement method proposed in the present invention and Fourier analysis are applicable and even in a case where a neuronal resonance signal has a random period and phase and has five times more noise than the corresponding MRI signal.

On the other hand, referring to FIGS. 2A to 2C again, frequency band selection filter characteristic mapping of neurons is described through the NR-MRI scheme according to an embodiment of the present invention.

According to an NR-MRI scheme of an embodiment of the present invention, as shown in FIG. 2A, the ME-GE, the SE-EPI, the GE schemes and imaging methods modified from the aforementioned three MRI pulse sequence types are tested. The SE-EPI and GE sequences are implemented by using separate NROG magnetic field.

In addition, as shown in FIG. 2B, multi-phase data is repetitively obtained and then the Fourier analysis is applied. In addition, a sliding-time window analysis is applied to the repetitive multi-phase data and a temporal change of the neuronal resonance frequency is observed. A target neuronal resonance frequency, namely, an oscillating frequency of the NROG magnetic field is applied to various ranges and observed, and various MRI image parameters are tested and optimized. At this time, the parameters to be optimized include the number of echoes, the number of gradient magnetic field pulses oscillating within one TR, the number of multi-phases, the magnitude of NROG magnetic field, an MRI pulse sequence type (ME-GE, SE-EPI, or GE) desired to image, and the magnitude of a main magnetic field of the MRI system.

All these researches are performed in the resting state and at the time of having external stimuli, and a frequency change between the resting state and the stimulated state is observed. The SE-EPI and GE sequences are used for observing a difference in spatial directivities of the neuronal resonance signal. Furthermore, the NR-MRI is compared with the existing fMRI, a resting-state fMRI and neuronal current measurement MRI schemes in various views (e.g., a temporal signal change, and spatial signal distribution, and the like).

According to the NR-MRI scheme of an embodiment of the present invention, as shown in FIG. 2A, the NROG magnetic field pattern may be implemented in the ME-GE, SE-EPI, and GE sequences. At this point, the number of multi-phases may be varied in a type of being increased from 4 to 16 by 4. The target neuronal resonance frequency is tested from 5 Hz to 500 Hz, and the frequency is varied by a relatively small interval in a low frequency band and by a wide interval in a high frequency band. At this point, the frequency band includes all of a theta wave (3.5 to 7.5 Hz), an alpha wave (7.5 to 12.5 Hz), and a beta wave (>12.5 Hz). The number of the ME-GE sequence and the number of NROG magnetic field pulses within one TR of the SE-PEI or GE sequence may be varied from 2 to 10. All other basic MRI parameters are optimized thereto. The optimization of these parameters is made by performing simulation and actual experiment in parallel.

The MRI experiment may be performed by mainly using a Sprague Dawley rat (SD-rat) having a weight of 200 to 500 g and using isoflurane for animal anesthetics.

In the NR-MRI according to an embodiment of the present invention, neuronal frequency characteristics according to a degree of anesthesia may be seen by testing in various isoflurane levels. At this point, electric stimulation may be applied in the following parameter ranges.

current=0.5-1.5 mA,
pulse duration=1-3 ms,
repetition rate=3-10 Hz,
stimulation duration=5-30 sec,
inter-stimulation period≥2 min.

The Fourier analysis is applied to the entire obtained data and also applied to the data divided in various time intervals (in a unit of from 10 seconds to 10 minutes), and then the temporal change of the neuronal resonance frequency may be seen. Such a temporal change of the neuronal resonance frequency may be evaluated over the entire brain.

The existing fMRi, the resting-state fMRI and the neuronal current measurement MRI schemes follow data acquisition and analysis methods published in advance. A basic imaging condition among imaging parameters of the NR-MRI scheme according to an embodiment of the present invention is maintained identically or similarly to the existing methods for fair comparison. A frequency distribution map of the brain, which is measured through the NR-MRI scheme in a resting state, is compared with a connectivity map obtainable through the existing resting-state fMRI, and a frequency distribution map of the brain, which is measured through the NR-MRI scheme in a state where electrical stimulation is present, is compared with the existing fMRI map. Comparing temporal changes of an NR-MRI signal according to an embodiment of the present invention and the existing fMRI signal, it may be helpful to verify that the NR-MRI signal is caused by direct neuronal resonance and not by blood flow dynamics.

The NR-MRI scheme according to an embodiment of the present invention is a first imaging method for directly and non-invasively measuring a neuronal electrical signal by using the MRI scheme in high resolution, and, at the same time, allowing frequency selective communication between brain regions to be researched. When the NR-MIR is successfully implemented, new information for researching the brain can be obtained and a significant effect can be brought to various brain related researches including neurology, psychology, and psychopathology. For example, how a communication frequency changes between the brain regions can be researched while the brain performs a specific work. In addition, it is also researched on what difference is between a normal person and a brain-related patient in communication frequency between the brain regions, and, through this, a communication frequency change may be also observed between specific brain regions, which may be a cause of brain diseases. A communication map over the entire brain can be completed according to a frequency, which significantly improves understanding of the brains of the normal person and the brain-related patient.

It is continuously revealed that numerous brain diseases are caused by communication between the brain regions. Various methods including various electrical and magnetic stimuli are attempted to treat the brain disease such as schizophrenia and Parkinson's disease. However, such treatments frequently accompany serious side effects. Such side effects may be caused by amplifying a wrong brain communication frequency and stimulating undesired brain regions.

Through the NR-MRI scheme according to the present invention, a desirable frequency may be found and a side effect occurred by stimulation in a wrong frequency band may be reduced.

On the other hand, the brain researches are considered very important in developed countries, and development of new image modality proposed in the NR-MRI scheme according to the present invention may be an absolute condition for leading a corresponding field.

The NR-MRI scheme according to the present invention is expected to suggest a new breakthrough in brain communication researches and diagnosis of brain related diseases.

Hereinafter, a method is described which processes an MRI signal according to an embodiment of the present invention with reference to FIG. 2. As an MRI scheme using the gradient magnetic field patterns 92 to 94 for detecting a magnetic field oscillation signal 96, the processing method, which is an MRI signal processing method using a process for obtaining MRI data ((iii) of FIG. 2C), may include acquiring a plurality of pieces of MRI data by repeating the process several times while changing relative phases ($\phi_1$, $\phi_2$, ..., $\phi_N$) between the gradient magnetic field pattern and the magnetic oscillating signal; and calculating frequency characteristics from the acquired plurality of pieces of MRI data. At this point, the plurality of pieces of MRI data may be K-space data or MRI image data. Here, the magnetic field oscillation signal may mean a signal about a magnetic field including a specific frequency component. In addition, the gradient magnetic field pattern may mean a signal about a magnetic field having a signal pattern including a certain frequency component. The MRI scheme using the gradient magnetic field pattern signal may mean an MRI scheme using a method for generating a gradient magnetic field by using the gradient magnetic field pattern signal. The relative phases may be easily defined between two signals when the gradient magnetic field pattern and the magnetic field oscillating signal are assumed to have an identical frequency.

At this point, the magnetic field oscillation signal may a signal having an unknown generation period and an unknown phase at a specific time.

At this point, the magnetic oscillating signal may include a specific frequency component (e.g., $f_{NO}$).

The pre-determined rule may be Fourier-transforming signals (e.g., 201 and 202 in FIG. 2C) of the acquired plurality of pieces of MRI data arrayed on a time-axis according to the relative phases.

At this point, the plurality of pieces of MRI data are temporally divided, and each of the divided data is Fourier-transformed to acquire time-axis data with respect to a neuronal signal change. For example, since the period of the magnetic field oscillating signal changes along the time, or since the magnetic oscillating signal is not generated in some time periods, the divided data may be used for grasping the changing pattern.

The pre-determined rule may be finding a value about the specific frequency (e.g., $f_{NO}$) among frequency components of the acquired plurality of pieces of MRI data.

The acquiring may include a acquiring process for acquiring N pieces of MRI data by repeating the process for the pre-determined N relative phases ($\phi_1$, $\phi_2$, ... $\phi_N$) between the gradient magnetic field pattern signal and the magnetic field oscillating signal, and differences between the N relative phases may satisfy integer multiples of $2*\pi/N$ with respect to the specific frequency.

A time to repeat (TR) among MRI parameters may be adjusted in order to make the differences between the N relative phases into integer multiples of $2*\pi/N$ with respect to the specific frequency.

At this point, the magnetic field oscillating signal may be a neuronal signal. The gradient magnetic field pattern may be an oscillatory gradient magnetic field pattern. The oscillatory gradient magnetic field pattern may be a bipolar readout gradient pattern using in an ME-GE imaging method.

In addition, spatial directivities of the gradient magnetic field pattern may be different with respect to two different repeatedly performed processes.

An MRI apparatus for performing the steps may be provided according to another embodiment of the present invention.

According to another embodiment, a computer-readable medium may be provided which has a program recorded thereon, which, when executed by an MRI apparatus, performs the steps.

According to another embodiment of the present invention, in order to detect a magnetic field oscillation signal having an unknown generation period and an unknown phase at a specific time, a magnetic resonance signal processing method may be provided which uses a process for obtaining MRI data with an MRI scheme using an oscillatory gradient magnetic field pattern signal having a pre-determined oscillation frequency. The method may use a first process including acquiring a plurality of pieces of MRI data by repeating the process a plurality of times while changing relative phases between the oscillatory gradient magnetic field pattern signal and the magnetic field oscillation signal; and calculating a value about the pre-determined oscillation frequency from the acquired plurality of pieces of MRI data according to a pre-determined rule. The method also includes acquiring P values about the pre-determined oscillation frequency with respect to the first process by performing the first process P times in order for the pre-determined oscillation frequency to have P different values.

According to NR-MRI scheme according to the present invention, the following three effect can be obtained.

Effect 1. Through the NR-MRI scheme, frequency band selection filter characteristics of neurons can be mapped. A frequency selective neuronal signal can be extracted by repetitively applying an MRI scheme into which a resonant gradient magnetic field pattern is grafted to multi-phases in comparison to a neuronal resonance frequency, obtaining an image, and applying a Fourier analysis. Such an imaging method can be applied to both a resting-state and a state where external stimuli are applied in order to check their difference, and can be compared with the existing MRI scheme.

Effect 2. A technique can be provided which performs systems biological researches on frequency selective communication mechanism between brain regions. Through this, the frequency selective communication mechanism between brain regions can be revealed through spiking neural network based neuronal modeling. In addition, interaction between an excitatory population, and an inhibitory population can be researched using neuronal population modeling such as a Wilson-Cowan model.

Effect 3. A technique can be provided which completes proof-of-concept and a frequency selective communication map between the entire brain regions. The proof-of-concept experiment may be performed (i) through an experiment simultaneously using the NR-MRI and electroencephalogram (EEG) and (ii) through applying the NR-MRI to a gene-manipulated rat. The technique can contribute to obtaining additional data for the proof-of-concept by grafting an experiment through the NR-MRI into systems biology based simulation and completing a frequency selective communication map between the entire brain regions.

According to the present invention, technology for maximizing a neuronal signal can be used by applying a gradient magnetic field pattern oscillating with a neuronal resonance frequency to an MRI scheme.

In addition, issues that an MRI signal by neuronal current is very small and that a neuronal resonance occurs randomly in temporal period and phase can be addressed by repetitively performing acquisition of multi-phase images and then extracting a component corresponding to the neuronal resonance frequency through Fourier analysis. Through these repetitive multi-phase image acquisition method and Fourier analysis, not only a neuronal signal can be frequency-selectively extracted, but also a signal-to-noise ratio (S/N ratio) can be significantly improved through a temporal averaging effect.

Furthermore, a communication channel map for each frequency band can be completed, which is unable with the existing schemes, and fundamental technology can be provided which can grasp a specific frequency related to brain functions and brain diseases and a corresponding brain region.

Although the present invention been described with reference to the specific embodiments, it is not limited thereto. Therefore, it will be readily understood by those skilled in the art that various modifications and changes can be made thereto without departing from the spirit and scope of the present invention defined by the appended claims. The contents of each of the claims herein can be combined to any other that is not dependent therefrom within an understandable scope through the specification.

What is claimed is:

1. A magnetic resonance signal processing method for detecting a magnetic field oscillation signal, the method comprising:
    obtaining N pieces of MRI (magnetic resonance imaging) data by repeating a step of obtaining an MRI data with an MRI scheme using a gradient magnetic field pattern N number of times while changing relative phases between the gradient magnetic field pattern and the magnetic field oscillation signal; and
    calculating a value related to an energy of a predetermined frequency component of an arranged signal produced by arranging the obtained N pieces of MRI data on a time-axis according to the relative phases,
    wherein the N pieces of MRI data are K-space data or the N pieces of MRI data are MRI image data.

2. The method of claim 1, wherein the magnetic field oscillation signal has an unknown generation period and an unknown phase at a specific time.

3. The method of claim 1, wherein the calculating comprises Fourier-transforming the arranged signal.

4. The method of claim 1, wherein the obtaining the N pieces of MRI data comprises repeating the step of obtaining an MRI data with the MRI scheme with respect to pre-determined N relative phases between the gradient magnetic field pattern and the magnetic field oscillation signal.

5. The method of claim 4, wherein the calculating comprises Fourier-transforming the arranged signal.

6. The method of claim 1, wherein the N pieces of MRI data are temporally divided and each of the divided data is Fourier-transformed to acquire time-axis data with respect to a magnetic field oscillation signal.

7. The method of claim 1, wherein, the obtaining the N pieces of MRI data comprises repeating the step of obtaining an MRI data with the MRI scheme with respect to pre-determined N relative phases between the gradient magnetic field pattern and the magnetic field oscillating signal, and
    a difference value between any two of the pre-determined N relative phases is an integral multiple of $2*pi/N$ with respect to an oscillation frequency of the gradient magnetic field pattern.

8. The method of claim 1, wherein a time to repeat (TR) among MRI parameters is adjusted for making the relative phases between the gradient magnetic field pattern and the magnetic field oscillation signal.

9. The method of claim 1, wherein the magnetic field oscillation signal is a neuronal signal.

10. The method of claim 1, wherein the gradient magnetic field pattern is an oscillatory gradient magnetic field pattern.

11. The method of claim 10, wherein the oscillatory gradient magnetic field pattern is a bipolar readout gradient pattern.

12. The method of claim 1, wherein spatial directivities of the gradient magnetic field pattern is different with respect to arbitrary two of the repeated steps of obtaining an MRI data with the MRI scheme.

13. An MM apparatus for detecting a magnetic field oscillation signal having an unknown generation period and an unknown phase at a specific time, the MRI apparatus being configured to perform;
    obtaining N pieces of MRI (magnetic resonance imaging) data by repeating a step of obtaining an MRI data with an MRI scheme using a gradient magnetic field pattern N number of times while changing relative phases between the gradient magnetic field pattern and the magnetic field oscillation signal; and
    calculating a value related to an energy of predetermined frequency component of an arranged signal produced by arranging the obtained N pieces of MRI data on a time-axis according to the relative phases.

14. A non-transitory computer readable medium having a program recorded thereon, which, when executed by an MRI apparatus, performs a method for detecting a magnetic field oscillation signal having an unknown generation period and an unknown phase at a specific time, the method comprising:
    obtaining N pieces of MRI (magnetic resonance imaging) data by repeating a step of obtaining an MRI data with an MRI scheme using a gradient magnetic field pattern N number of times while changing relative phases between the gradient magnetic field pattern and the magnetic field oscillation signal; and
    calculating a value related to an energy of a predetermined frequency component of an arranged signal produced by arranging the obtained N pieces of MRI data on a time-axis according to the relative phases.

* * * * *